Aug. 12, 1958 T. E. MOTOSE Plant Pat. 1,740
ROSE PLANT
Filed Dec. 10, 1957
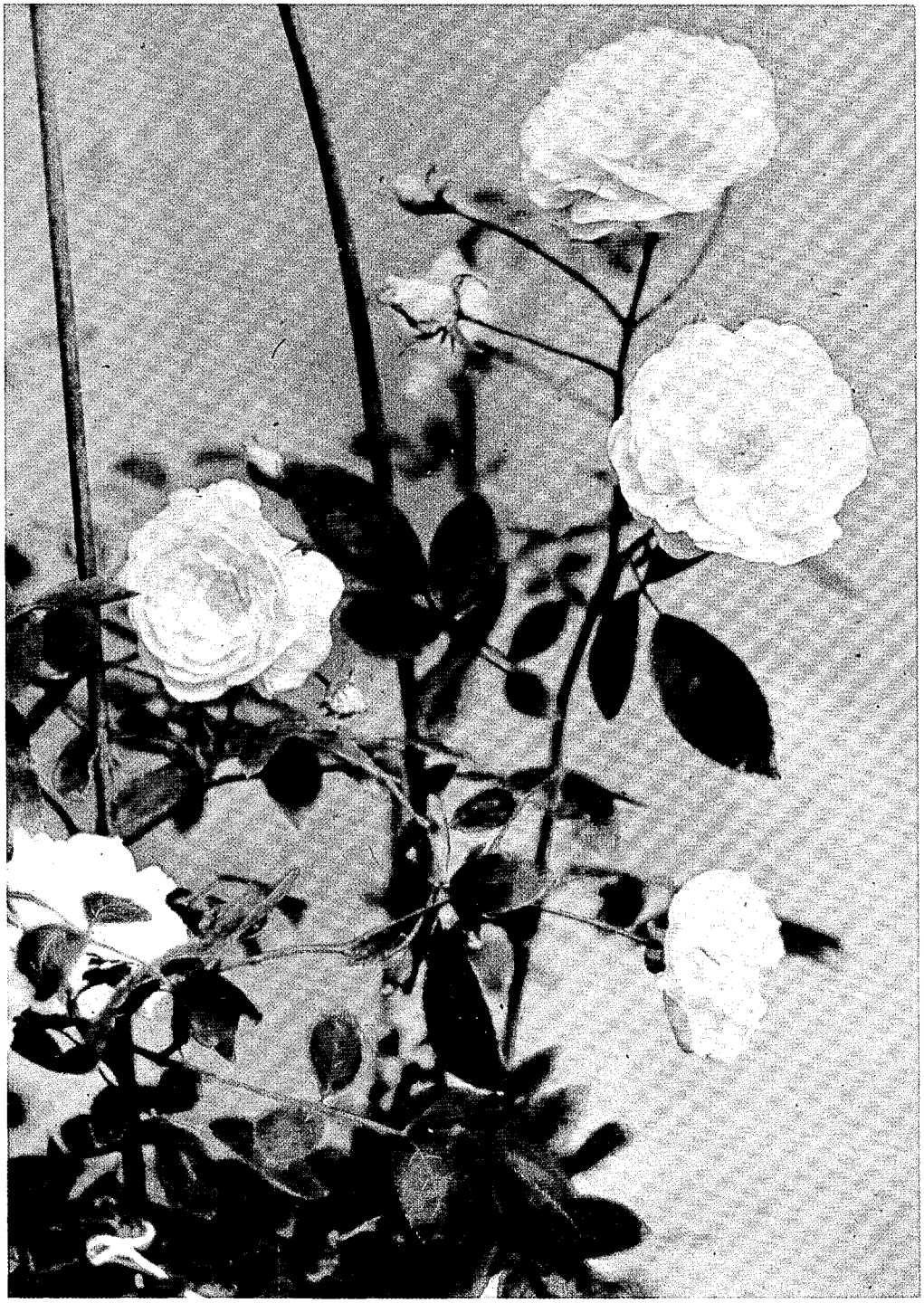
Inventor: Thomas Edison Motose United States Patent Office Plant Pat. 1,740

Patented Aug. 12, 1958

1,740

ROSE PLANT

Thomas Edison Motose, Fairport, N. Y., assignor to George B. Hart, Inc., Rochester, N. Y., a corporation of New York Application December 10, 1957, Serial No. 701,949

1 Claim. (Cl. 47—61)

This invention relates to a new and distinct variety of rose plant, originating as a cross of the tall climbing variety of Summer Snow, known as Climbing Summer Snow (Plant Patent No. 400) and the low bush variety of Summer Snow, known as Summer Snow (Plant Patent No. 416).

In making this cross, I had for my object the origination of a new hardy variety of rose plant bearing flowers of a color other than plain white, and adaptable for outdoor gardens of the northern States. Both parents of this cross are white flowering roses. Since the original parent of the two Summer Snows was a rambler known as Tausendschon (not patented), a multi-colored rose, I presumed that the white flowering Summer Snows carried a pink or a yellow coloring as a recessive characteristic in their germ cells.

Numerous crosses of the two varieties of Summer Snows were made. The majority of the seedlings turned out to be white flowering sort. There were some seedlings with light pink cast on their petals, but the floral form was nothing like that of the white flowering Summer Snow. Finally, after numerous trials, I obtained a seedling possessing a new characteristic, beautiful pink coloring in its blooms, and with floral form and size identical to those of the white flowering Summer Snows.

DIFFERENTIATING CHARACTERISTICS

Both parents of this new rose are recognized in the horticultural world as distinct varieties, each with characteristics peculiar to itself.

This new variety possesses the following characteristics, which, when considered individually and in combination, make it different from both of its parents and other roses:

(*a*) No thorns on its canes and branches as a rule;

(*b*) Produces a larger number of lateral canes or branches than its parents;

(*c*) Pink coloring of its blooms which can be easily differentiated from the white and off-shade colorings of those of its parents;

(*d*) Tendency to grow taller than its pollen parent (the bush type) and less than one-fourth the height of its seed parent (the climbing type) at corresponding age; and (*e*) Larger quantity of blooms than its parents as observed in Shrub Oak, N. Y. and Fairport, N. Y.

PLACE OF ORIGIN

This new variety was originated in the incorporated Village of Yorktown, County of Westchester, State of New York.

ASEXUAL REPRODUCTION

Tests conducted in my private experimental gardens in Shrub Oak, N. Y. and Fairport, N. Y. during a period of five years prior to this first public description, have shown that this new variety's characteristics described in the preceding paragraphs and to be described in detail in the succeeding pages, are fully and definitely established and that the said characteristics and the combinations thereof are transmissible asexually, such as by budding, grafting, layerage or cutting.

PICTURE OF THE NEW VARIETY

The accompanying picture of this new variety shows the shape, relative size and colors of its various parts, as seen in natural light on a fair day in late August, 1957, Fairport, N. Y. There is little or no differentiating features in the very young leaves, immature buds and very old blooms, and no special effort has been made to illustrate or color them in detail other than those appearing incidentally in the picture.

In making this picture, I have used the best available colors, but due to the very nature of color pigments the colors on this picture may, in time, change like those on any other picture or painting. The correct colors of this new variety's canes, foliage and blooms are the ones described or named specifically in words and numerals, and not the ones that might appear on said picture in future years.

THE COLORS OF THE LIVING TISSUES

The colors of the various parts of this new variety are those observed in fair weather in daylight during the later part of August, 1957, in Fairport, N. Y.

The living colors of this new variety, like those of any other living plant, are effected by temperature, humidity, soil condition, chemical fertilizers, relative duration of diurnal and nocturnal periods, and other known and unknown factors, and therefore shall undergo appreciable changes from time to time. But the changes in this new variety are so slight that each color variation shall remain within its general color boundary.

The colors specifically named and described in words and numerals in this specification are those seen without glass obstruction in daylight by person of normal eyesight. Whenever the colors as seen on this new variety in an unobstructed daylight and the colors as seen on it under glass obstruction or in artificial light do not agree, the colors as seen in unobstructed daylight and described in words and numerals in this specification are the correct colors of this new variety.

The color terminology used in describing the new variety is in accordance to Ridgway's Color Standard and Nomenclature (whenever the plate number followed by the abbreviation "Ridg." is given), Horticultural Color Charts of the British Color Council (whenever the plate number followed by the abbreviation "Hort." is given), or general meaning of Webster's Dictionary (when plate number is absent). The Horticultural Color Charts are used when Ridgway's Color Standard does not quite describe the actual specimen, and vice versa.

PLACE AND TIME OF OBSERVATION

Observations were made in Fairport, N. Y., during the later part of August, 1957, for the specific purpose of compiling data for this specification.

DETAILED DESCRIPTION

The following is a detailed description of this new variety:

(1) *Parentage*

A seedling originated as a cross of a tall climbing hybrid polyantha rose known as Climbing Summer Snow (seed parent) and a bush type hybrid polyantha rose known as Summer Snow (pollen parent). The two parents are patented varieties: seed parent Pat. 400, pollen parent Pat. 416.

(2) *Classification*

*Botanic.*—A shrub or woody perennial plant belonging to the continuous or recurrent blooming hybrid variety of the cultivated species of the genus Rosa.

*Commercial.*—A bush type hybrid polyantha rose plant.

(3) *Plant as a whole*

*Form.*—Bushy and well branched.

*Growth.*—Fast growing and vigorous.

*Height at maturity.*—3 to 4 feet, as observed in Fairport, N. Y.

(4) *Canes and stems*

*Very young canes and stems.*—Smooth, slender and Oil Green (Plate No. 5 Ridg.).

*Young canes.*—Smooth bark, Oil Green (Plate No. 5 Ridg.).

*Mature or near mature canes.*—Smooth bark, Bice Green (Plate No. 17 Ridg.).

*Old canes.*—Smooth bark (rarely fissued), Spinach Green (Plate No. 5 Ridg.) and sometimes light green.

(5) *Thorns and prickles*

No thorns on its canes, branches and stems as a general rule.

Very small and inconspicuous "prickles" on the under side of petioles and petiolules.

(6) *Foliages*

*Leaflet.*—Small and almost equally pointed at both ends; its greatest width at about its mid-section; its length about twice the dimension of its greatest width, and frequently more.

*Leaf.*—A compound of five or seven leaflets. (Some seasons, it has more leaves composed of 5 leaflets, while at other times more leaves with 7 leaflets. The cause of this phenomenon has not been ascertained.)

*Texture.*—Smooth on the obverse or upper side, and slightly leathery on the reverse or under side.

*Serrations.*—Evenly marked but not conspicuous; single form as a general rule.

*Stipules.*—Small and very inconspicuous.

*Auricles.*—Small, left and right tips unbranched as a rule.

*Petioles and petiolules.*—Small and slender.

*Colors.*—Light Greenish Yellow (Plate No. 5 Ridg.) on both sides, and occasional overcast of light pink, when young; Scheele's Green (Plate No. 6, Ridg.) on both surfaces, with the under surface occasionally becoming Light Greenish Yellow (Plate No. 5 Ridg.) when older but before maturity; Spinach Green (Plate No. 5 Ridg.) on the upper side, and Scheele's Green (Plate No. 6 Ridg.) and sometimes Lavender Green (Plate No. 000761/1 Hort.) on the under surface when mature.

*Quantity.*—About the same as that of *Rosa multiflora* foliage.

(The words "side" and "surface" are used synonymously in describing the foliage.)

(7) *Flowering bud*

*Size.*—Small.

*Shape.*—Ovoid, with a pointed tip when tightly closed.

*Color of visible petal when sepals first begin to divide.*—Various shades of pink, with Bengal Rose (Plate No. 25/3 Hort.) predominating.

*Color of visible petals when sepals further divide.*—Bengal Rose (Plate No. 25/3 Hort.) as a rule, and Tyrian Rose (Plate No. 24/3 Hort.) on some occasions.

*Color of visible petals when half blown.*—Bengal Rose (Plate No. 25/3 Hort.) as a general rule, and Tyrian Rose (Plate No. 24/3 Hort.) on some occasions.

*Color or general appearance of flowering buds from a distance of 10 or 15 feet in average daylight.*—Soft, medium pink when partly opened.

*Pedicel.*—Short, slender and slightly rough; Bice Green (Plate 17 Ridg.).

*Peduncle.*—Short, less rough than the pedicel; Bice Green (Plate No. 17 Ridg.).

*Sepals.*—Slightly serrated, Light Bice Green (Plate No. 17 Ridg.) inside and Bice Green (Plate No. 17 Ridg.) outside.

*Calyx.*—Small, smooth, Bice Green (Plate No. 17 Ridg.).

*Opening characteristic.*—Opens up very well even in rainy season, with no tendency to remain closed in ball shape.

(8) *Flower*

*Size.*—Two to two and one-half inches in diameter when fully opened.

*Quantity to a flowering branch or flowering stem.*—Quite frequently one to a stem, and also quite frequently in clusters of 2, 3 or more.

*Shape when fully opened.*—Identical to that of the bloom of Summer Snow at the same stage and may be described as resembling the convex face of a pocket watch (time-piece) of equivalent diameter, but with a slight depression in the central area.

*Petalage.*—30 to 35 as a general rule, and sometimes more.

*Fragrance.*—A mild, sweet fragrance resembling that of Summer Snow.

*Color of bloom when about one-half to three-fourths open, as viewed from above.*—Bengal Rose (Plate No. 25/3 Hort.) as a general rule, and perceptibly lighter shade on some occasions.

*Color of bloom when one-half to three-fourths open, as viewed from below.*—The general color of the upper surface of the petal of Alberta peach bloom, gradually becoming a lighter shade of pink towards the base of corolla.

*Color of bloom when fully opened, but still fresh, as viewed from above.*—Rose Bengal (Plate No. 25/3 Hort.), excepting the small area in the center, in normal weather during growing seasons in Fairport, N. Y.; Tyrian Rose (Plate No. 24/3 Hort.) in adverse weather.

*Color of bloom when fully opened, but still fresh, as viewed from below.*—General color of the upper surface of Alberta peach bloom, gradually becoming a lighter shade of pink resembling the general coloring of fresh apple blossoms toward the base of corolla.

*General coloring at the end of 6th or 7th day of bloom.*—Light pink turning to pinkish cream, or cream overcast with light pink. (The discoloration due to the advanced age of the bloom does not follow or remain reasonably long enough in any definite color category that can be specifically identified in terms of Horticultural Color Chart or Ridgway's Color Standard since the whole transition is erratic and ephemeral at the mercy of weather.)

*General appearance and color of the cluster of blooms as viewed from a distance of about 25 feet in daylight during the height of bloom.*—Delicate looking, clear pink—easily distinguishable from the shapes and colors of other polyantha, floribunda or hybrid polyantha, including the Climbing Summer Snow and the Summer Snow.

*Lasting quality.*—Longer than that of the average hybrid tea bloom, and equal to or a little longer than that of the average floribunda bloom.

(9) *Petals*

*Appearance.*—Satiny on both sides.

*Shape of outer petals.*—Cordate in general pattern, without dentation as a general rule, with the acute end attached and the obtuse side free.

*Shape of middle petals.*—Ovate with the acute tip attached.

*Shape of inner petals.*—Cuneate with the acute tip attached.

*Arrangement.*—Irregular.

*Color of the upper surface.*—Rose Bengal (Plate No. 25/3 Hort.) as a general rule, and occasionally Tyrian Rose (Plate No. 24/3 Hort.).

*Color of the under surface.*—The area towards the obtuse side (roughly three-fourths of the total area) identical or closely resembling the general coloring of the upper surface of Alberta peach petal; the area towards the acute side (a little less than one-fourth of the total area) identical or resembling the general coloring of fresh apple blossom.

*Color of the area close to the acute end.*—Very light yellow or cream, depending upon the season and weather.

*Persistence.*—Drops off cleanly as a general rule in most weather conditions.

*Texture.*—Smooth.

*Thickness.*—Thin.

*Veins.*—Inconspicuous.

(10) *Genital organs*

*Stigmas.*—Small in size, Straw Yellow (Plate No. 604/3 Hort.), and occasionally very pale yellow, on the underside and rim of orifice.

*Style.*—Small in size, short in height, very pale yellow or closely related color.

*Pollens.*—Abundant in quantity, and Orange Yellow (Plate No. 3 Ridg.) or very closely related color.

*Anthers.*—Small in size, and Orange Yellow (Plate No. 3 Ridg.) in color.

*Filaments.*—Small in size, uneven in height, Straw Yellow (Plate No. 604/3 Hort.) as a general rule, but sometimes of much lighter shade of yellow.

*Ovaries.*—All enclosed.

(11) *Hips*

*Shape.*—Almost spherical.

*Size.*—Small, one to one and one-fourth centimeters in diameter.

*Color when mature.*—Orange red or closely related color.

(12) *Cell structure*

*Type.*—Polyploid.

(13) *Frequency of flowering*

Recurrent or continuous when in good health.

(14) *Quantity of blooms*

Abundant as observed in Fairport, N. Y.

(15) *Hardiness*

It is sufficiently hardy as to survive with ease the winter weather of Fairport, N. Y., when given the customary soil and straw protections generally given to hybrid tea and hybrid polyantha roses of this region.

I claim:

A new and distinct variety of hybrid polyantha rose plant classified botanically as, and belonging to, the continuous or recurrent blooming variety of the cultivated species of the genus Rosa, characterized as to novelty by its thornless canes and branches, by its tendency to produce large number of lateral branches, by its small and narrow leaflets, by the clear pink coloring of its blooms, by its great production of blooms, by its distinctive floral pattern, and by the combination of all the said characteristics, substantially as herein described and illustrated.

No references cited.